United States Patent
Nakano et al.

(10) Patent No.: US 6,479,646 B1
(45) Date of Patent: Nov. 12, 2002

(54) METALLOCENE COMPOUNDS HAVING INDENYL LIGAND AND CATALYSTS FOR OLEFIN POLYMERIZATION CONTAINING THE SAME

(75) Inventors: Masato Nakano, Ichihara (JP); Tsutomu Ushioda, Ichihara (JP); Seiki Mitani, Ichihara (JP); Hiroshi Yamazaki, Tokorozawa (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 0 days.

(21) Appl. No.: 09/686,619

(22) Filed: Oct. 12, 2000

(30) Foreign Application Priority Data

Oct. 22, 1999 (JP) .............................. 11-300857
May 19, 2000 (JP) ....................... 2000-148867

(51) Int. Cl.[7] .......................... B05J 31/00; B05J 37/00; C08F 4/02; C08F 4/60
(52) U.S. Cl. .............................. 534/10; 534/11; 534/14; 534/15; 556/47; 556/143; 562/428; 502/117
(58) Field of Search .................. 534/7, 10–16; 502/100, 102, 103, 117; 556/47, 143, 11; 562/428

(56) References Cited

U.S. PATENT DOCUMENTS 5,585,509 A * 12/1996 Langhauser et al. .......... 556/11
5,756,608 A * 5/1998 Langhauser et al. ......... 526/127

FOREIGN PATENT DOCUMENTS

| JP | 7-96566 | 10/1995 |
| JP | 7-258282 | 10/1995 |
| JP | 8-12715 | 1/1996 |
| JP | 8-183814 | 7/1996 |
| JP | 9-510745 | 10/1997 |

OTHER PUBLICATIONS

Jennifer L. Maciejewski Petoff, et al., "Elastomeric Polypropylene From Unbridged 2–Arylindenyl Zirconocenes: Modeling Polymerization Behavior Using ANSA–Metallocene Analogues", J. Am. Chem. Soc., vol. 120, No. 44, 1998, pp. 11316–11322.

Ewen "Polymerization Catalysts with Cyclopentadienyl Ligands Ring–Fused to Pyrrole and Thiophene Heterocycles", J. Am. Chem. Soc., vol. 120, No. 41, 1998, pp. 10786–19787.

Maurizio D'Auria, "Photochemical Coupling Between Indene and Nitroarenes", Tetrahedron Letters, vol. 35, No. 4, 1994, pp. 633–636.

Thorsten Dreier, et al., "Heteroaromatic–Substituted Indenyl Complexes of Zirconium", 218th ACS National Meeting, New Orleans, Aug. 22–26 (1999), 1 page.

Nicole Schneider, et al., "Zirconocene Complexes With Cyclopental[ι]Phenantherene Ligands: Syntheses, Structural Dynamics, and Properties as Olefin Polymerization Catalysts", Organometallics, vol. 19, No. 18, (2000), pp. 3597–3604.

* cited by examiner

Primary Examiner—Dameron L. Jones
(74) Attorney, Agent, or Firm—Oblon, Spivak, McClelland, Maier & Neustadt, P.C.

(57) ABSTRACT

A metallocene compound having an indenyl ligand substituted by a heteroaromatic group, which is useful as an olefin polymerization catalyst. The metallocene compound has the following structure

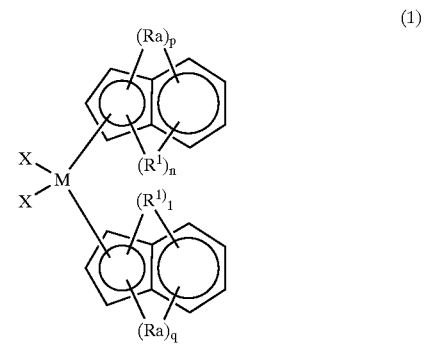

(1)

wherein M is a transition metal atom;

each Ra is a monocyclic or polycyclic heteroaromatic group;

each $R^1$ is halogen, a hydrocarbon group of 1–20 carbons, a halogenated hydrocarbon group of 1–20 carbons, etc., or adjacent $R^1$'s may be joined together to form a ring of 6–8 carbons; p and q are each 1–7; n and l are each 0 or 1–6;

and each X is halogen, a hydrocarbon group of 1–20 carbons, a halogenated hydrocarbon group of 1–20 carbons, etc.

20 Claims, No Drawings

METALLOCENE COMPOUNDS HAVING INDENYL LIGAND AND CATALYSTS FOR OLEFIN POLYMERIZATION CONTAINING THE SAME

FIELD OF THE INVENTION

This invention relates to new metallocene compounds useful as a catalyst component for olefin polymerization. More particularly, the invention relates to metallocene compounds having an indenyl ligand substituted by a heteroaromatic group and catalysts for olefin polymerization containing said metallocene compounds.

BACKGROUND OF THE INVENTION

As a catalyst component which can be used in the polymerization of olefins, conventional Ziegler-Natta catalysts have been partly replaced by the metallocene compounds wherein a multidentate compound containing a π-electron donor such as unsubstituted or substituted cycloalkadienyl groups is coordinated to a transition metal atom, said cycloalkadienyl groups including, e.g., unsubstituted or substituted cyclopentadienyl, indenyl, tetrahydroindenyl and fluorenyl groups.

In recent years, various metallocene compounds having an improved olefin polymerization activity per mole of a transition metal atom have been proposed. It is known that polymers of α-olefin having high stereoregularity, in particular, propylene polymers having high stereoregularity can be preferably prepared by using a metallocene compound having a $C_2$ symmetry as a catalyst component, wherein a multidentate compound having two substituted cycloalkadienyl groups bonded with a divalent linking group is coordinated to a transition metal atom (J. Am. Chem. Soc. 1998, 120, 11316–11322).

Further, the development of metallocene compounds with a high olefin polymerization activity has been continued. Various metallocene compounds have been proposed wherein a heteroatom is introduced into the substituent or the cycloalkadiene ring in the substituted cycloalkadienyl group. For instance, Japanese Patent Kokai 7-258282 discloses metallocene compounds wherein two indenyl ligands are linked to each other through a linking group and a saturated group containing a heteroatom such as nitrogen, phosphorus, arsenic, antimony or bismuth is directly linked to a carbon group at the 2-position of the indenyl groups through the heteroatom, and specifically, dimethylsilanediylbis(2-pyrrolidino-1-indenyl)zirconium dichloride.

Japanese Patent Kokai 8-183814 discloses metallocene compounds wherein two indenyl ligands are linked to each other through a linking group and the indenyl ligand is substituted by a 1-pyrrolyl group, a 1-indolyl group or the like at the 4-position, and specifically, dimethylsilylenebis(4-(1-indolyl)-2-methylindene)zirconium dichloride.

J. Am. Chem. Soc. 1998, 120, 10786–10787 discloses metallocene compounds wherein a heteroatom-containing cycloalkadiene having a thiophene ring or a pyrrol ring condensed to a cyclopentadiene ring is linked through a divalent linking group and coordinated to a transition metal atom.

Japanese Patent Publication 9-510745 discloses bis(2-phenylindenyl)zirconium dichloride as a non-bridged indenyl complex capable of producing a stereo block polypropylene which is a elastomeric polyolefin.

DISCLOSURE OF THE INVENTION

Elastomeric polyolefins having a rubber elasticity have attracted the attention of those skilled in the art recently. A new catalyst for efficiently producing elastomeric polyolefins has been desired, but the conventional catalysts as mentioned above do not meet the demands.

An object of the present invention is to provide a catalyst for efficiently producing elastomeric polyolefins having a high heat resistance.

The present inventors have made earnest studies to accomplish the above object and found that elastomeric polyolefins can be produced efficiently by using as a catalyst component metallocene compounds having two indenyl ligands wherein the indenyl ligand is substituted by a heteroaromatic group preferably at a specific position, and also that elastomeric polyolefins with a high heat resistance can be produced efficiently by using as a catalyst component metallocene compounds wherein the indenyl ligand is substituted by a furyl group at the 2-position.

The present invention relates to a metallocene compound having an indenyl ligand represented by the following formula (1)

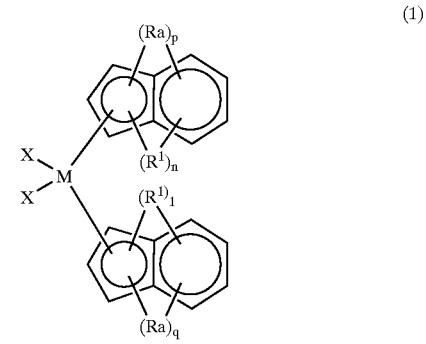

wherein M represents a transition metal atom in Group 3 including lanthanoid and actinoid series, or Group 4 or 5 of the periodic table;

each Ra independently represents a monocyclic or polycyclic heteroaromatic group containing a heteroatom selected from the group consisting of an oxygen atom, a sulfur atom and a nitrogen atom;

each $R^1$ independently represents a halogen atom, a hydrocarbon group of 1–20 carbons, a halogenated hydrocarbon group of 1–20 carbons, a silyl group substituted by said hydrocarbon group or said halogenated hydrocarbon group, an amino group substituted by said hydrocarbon group, or a monocyclic or polycyclic amino group, and adjacent $R^1$'s may be joined together to form a ring of 6–8 carbons;

p and q are each independently an integer of 1–7;

n and l are each independently 0 or an integer of 1–6; and

X each independently represents a halogen atom, a hydrocarbon group of 1–20 carbons, a halogenated hydrocarbon group of 1–20 carbons, or a silyl group substituted by said hydrocarbon group or said halogenated hydrocarbon group; and a catalyst for olefin polymerization comprising said metallocene compound.

DETAILED DESCRIPTION OF THE INVENTION

In the formula (1) which represents the metallocene compounds of the present invention, M represents a transition metal atom in Group 3 including lanthanoid and actinoid series, or Group 4 or 5 of the periodic table, and preferably, titanium, zirconium or hafnium.

Each Ra independently represents a monocyclic or polycyclic heteroaromatic group containing a heteroatom selected from the group consisting of an oxygen atom, a sulfur atom and a nitrogen atom, which links to the 5- or 6-membered ring of the indenyl ligand. For example, the monocyclic or polycyclic heteroaromatic groups containing an oxygen atom can include furyl and benzofuryl, and furyl groups can include 2-furyl and 3-furyl.

The monocyclic or polycyclic heteroaromatic groups containing a sulfur atom can include thienyl and benzothienyl, and thienyl groups can include 2-thienyl and 3-thienyl.

The monocyclic or polycyclic heteroaromatic groups containing a nitrogen atom can include pyrrolyl, pyridyl, indolyl and quinolyl. Pyrrolyl groups can include 1-pyrrolyl, 2-pyrrolyl and 3-pyrrolyl; pyridyl groups can include 2-pyridyl, 3-pyridyl and 4-pyridyl; indolyl groups can include 1-indolyl and 3-indolyl; and quinolyl groups can include 1-quinolyl and 3-quinolyl.

The heteroaromatic group Ra may be substituted by a substituent such as an alkyl group, an aryl group, an aralkyl group, an alkoxy group, a substituted silyl group and a halogen atom. The adjacent substituents may be joined together to form a condensed ring. Typical examples of the substituents can include methyl, ethyl, tert-butyl, phenyl, vinyl, methoxy, trimethylsilyl, vinyldimethylsilyl, phenyldimethylsilyl, methoxydimethylsilyl and fluoro. A typical example of the condensed ring is a benzene ring.

Preferable heteroaromatic groups are 2-furyl, 3-furyl, 2-thienyl, 3-thienyl, 2-pyrrolyl, 3-pyrrolyl, 2-pyridyl, 3-pyridyl, 4-pyridyl, benzofuryl, benzothienyl, 3-indolyl, 1-quinolyl and 3-quinolyl. More preferable is furyl and particularly preferable is 2-furyl.

Unsubstituted or substituted 2-furyl groups can include 2-furyl, 2-(5-methyl)furyl, 2-(5-t-butyl)furyl, 2-(5-trimethylsilyl)furyl, 2-(5-phenyl)furyl, 2-(5-vinyldimethylsilyl)furyl, 2-(4,5-benzofuryl), 2-(4,5-dimethyl)furyl and 2-(5-fluoro)furyl. For the production of elastomeric polyolefins with a high heat resistance, it is preferable that at least one of these heteroaromatic groups is linked to the 5-membered ring of the indenyl ligand. More preferably, the heteroaromatic group is linked at the 2-position of the indenyl ligand.

Preferable metallocene compounds of the present invention are the compounds of the formula (1) wherein two heteroaromatic group Ra's are furyl and each furyl group is bonded at the 2-position of two indenyl ligands.

More preferable metallocene compounds of the present invention are the compounds of the formula (1) wherein two heteroaromatic group Ra's are furyl and each furyl group has the substituent and is further bonded at the 2-position of two indenyl ligands. Preferable metallocene compounds for the production of highly stereoregular olefin polymers are those wherein the substituent is bonded at the 5-position of the furyl group. Most preferable metallocene compounds are those wherein each furyl group bonded at the 2-position of two indenyl ligands has a substituent at the 5-position. Typical Examples of the substituents can include an alkyl group, an aryl group, an aralkyl group, an alkoxy group, a substituted silyl group and a halogen atom, and more specifically, methyl, ethyl, tert-butyl, phenyl, vinyl, methoxy, trimethylsilyl, vinyldimethylsilyl, phenyldimethylsilyl, methoxydimethylsilyl and fluoro. Further, the adjacent substituents may be joined together to form a condensed ring, a typical example of which is a benzo ring.

Most preferable furyl groups wherein the substituent is bonded at the 5-position can include 2-(5-methyl)furyl, 2-(5-t-butyl)furyl, 2-(5-phenyl)furyl, 2-(5-trimethylsilyl)furyl, 2-(5-vinyldimethylsilyl)furyl, 2-(4,5-benzofuryl), 2-(4,5-dimethyl)furyl and 2-(5-fluoro)furyl.

Each $R^1$ independently represents a halogen atom, a hydrocarbon group of 1–20 carbons, a halogenated hydrocarbon group of 1–20 carbons, a silyl group substituted by said hydrocarbon group or said halogenated hydrocarbon group, an amino group substituted by said hydrocarbon group, or a monocyclic or polycyclic amino group.

The halogen atoms can include, e.g., fluorine, chlorine, bromine and iodine.

The hydrocarbon groups of 1–20 carbons can include an alkyl group of 1–20 carbons, an aryl group of 6–20 carbons, an aralkyl group of 7–20 carbons, an alkoxy group of 1–20 carbons, an aryloxy group of 6–20 carbons and an aralkyloxy group of 7–20 carbons.

The alkyl groups of 1–20 carbons can include straight- or branched-chain alkyl groups, for example, methyl, ethyl, propyl, i-propyl, n-butyl, i-butyl, tert-butyl, sec-butyl, pentyl, hexyl, heptyl, octyl, 2-ethylhexyl, nonyl, decyl, dodecyl and octadecyl, and cyclic alkyl groups which may be substituted by said chain alkyl groups, for example, cyclopropyl, cycloheptyl and cyclohexyl.

The aryl groups of 6–20 carbons can include, for example, phenyl, naphthyl and anthryl; and those groups which are further substituted by said alkyl group, for example, tolyl, xylyl and trimethylphenyl.

The aralkyl groups of 7–20 carbons can include, for example, benzyl, naphthylmethyl and anthrylmethyl; and those groups which are further substituted by said alkyl group, for example, (methylphenyl)methyl, (dimethylphenyl)methyl, (trimethylphenyl)methyl, (ethylphenyl)methyl, (propylphenyl)methyl and (butylphenyl)methyl.

The alkoxy groups of 1–20 carbons can include chain and cyclic alkoxy groups having said alkyl group, for example, methoxy, ethoxy, propoxy, isopropoxy, butoxy, t-butoxy, hexyloxy and cyclohexyloxy.

The aryloxy groups of 6–20 carbons can include substituted or unsubstituted aryloxy groups having said aryl group, for example, phenoxy, naphthyloxy and anthryloxy.

The aralkyloxy groups of 7–20 carbons can include, for example, aralkyloxy groups having said aralkyl groups such as benzyloxy.

The halogenated hydrocarbon groups of 1–20 carbons can include halogenated alkyl groups, halogenated aryl groups, halogenated aralkyl groups, halogenated alkoxy groups, halogenated aryloxy groups and halogenated aralkyloxy groups, for example, monochloromethyl, dichloromethyl, trichloromethyl, perfluoroethyl, monochlorophenyl, difluorophenyl and monochlorobenzyl.

The silyl groups substituted by said hydrocabon groups can include those which are tri-substituted by said hydrocarbon group, e.g., trimethylsilyl, triethylsilyl, triphenylsilyl, tribenzylsilyl, triethoxysilyl and dimethylphenoxysilyl. The silyl groups substituted by said halogenated hydrocarbon groups can include (trifluoromethyl)dimethylsilyl, (fluorophenyl)dimethylsilyl, and (chloromethyl)dimethylsilyl.

The amino groups substituted by said hydrocarbon groups can include those which are di-substituted by said hydrocarbon groups, for example, dimethylamino, diethylamino and methylethylamino. The monocyclic amino groups may be saturated or unsaturated, which can include, e.g., 1-pyrrolidyl and 1-pyrrolyl. The polycyclic amino groups may be saturated or unsaturated, which can include, e.g., 1-indolyl.

In the metallocene compounds of the present invention, it is preferable that the substituent $R^1$ on the indenyl group is aryl or benzo, because olefin polymers of higher molecular weight can be produced. It is especially preferable that aryl or benzo is introduced at the 4-position of the indenyl group. Examples of such substituents can include 4-phenyl, 4-naphthyl and 4,5-benzo.

p and q represent the number of Ra and each is independently an integer of 1–7, preferably 1–3.

n and l represent the number of $R^1$ and each is independently 0 or an integer of any one of 1–6, preferably 0 or an integer of any one of 1–4.

X each independently represents a halogen atom, a hydrocarbon group of 1–20 carbons, a halogenated hydrocarbon group of 1–20 carbons, or a silyl group substituted by said hydrocarbon group or said halogenated hydrocarbon group. Each X has the same definition as defined above for $R^1$, but X and $R^1$ are independent from each other. X is preferably a halogen atom, and more preferably chlorine.

Non-limitative examples of the metallocene compounds according to the present invention can include bis(2-(2-furyl)indenyl)zirconium dichloride, bis(2-(2-furyl)indenyl)zirconium dibromide, bis(2-(2-furyl)indenyl)zirconium methylchloride, bis(2-(2-furyl)indenyl)zirconium diemthyl, bis(2-(2-furyl)indenyl)zirconium diphenyl, bis(2-(2-thienyl)indenyl)zirconium dichloride, bis(2-(N-pyrrolyl))indenyl)zirconium dichloride, bis(2-(2-pyridyl)indenyl)zirconium dichloride, bis(2-(2-benzofuryl)indenyl)zirconium dichloride, bis(2-(2-indolyl)indenyl)zirconium dichloride, bis(2-(2-quinolyl)indenyl)zirconium dichloride, bis(2-(2-furyl)-1-methylindenyl)zirconium dichloride, bis(2-(2-furyl)-4-methylindenyl)zirconium dichloride, bis(2-(2-furyl)-4-phenylindenyl)zirconium dichloride, bis(2-(2-furyl)-4-naphthylindenyl)zirconium dichloride, bis(2-(2-furyl)-4,5-benzoindenyl)zirconium dichloride, bis(2-(2-furyl)cyclopentaphenanthryl)zirconium dichloride, bis(2-(2-furyl)4-phenyl-7-methyl-indenyl)zirconium dichloride, bis(2-(2-(5-trimethylsilyl)furyl)indenyl)zirconium dichloride, bis(2-(2-(5-vinyldimethylsilyl)furyl)indenyl)zirconium dichloride, bis(2-(2-(5-phenyl)furyl)indenyl)zirconium dichloride, bis(2-(2-(5-methyl)furyl)indenyl)zirconium dichloride, bis(2-(2-(4,5-dimethyl)furyl)indenyl)zirconium dichloride, bis(2-(2-(5-trimethylsilyl)furyl)-4-phenylindenyl)zirconium dichloride, bis(2-(2-(5-trimethylsilyl)furyl)-4,5-benzoindenyl)zirconium dichloride, bis(4-(2-furyl)-2-phenylindenyl)zirconium dichloride, bis(4-(1-pyrrolyl)-2-phenylindenyl)zirconium dichloride, bis(4-(1-indolyl)-2-phenylindenyl)zirconium dichloride, bis(2-(2-furyl)indenyl)hafnium dichloride, bis(2-(2-furyl)indenyl)hafnium dibromide, bis(2-(2-furyl)indenyl) hafnium methylchloride, bis(2-(2-furyl)indenyl)hafnium dimethyl, bis(2-(2-furyl)indenyl)hafnium diphenyl, bis(2-(2-thienyl)indenyl)hafnium dichloride, bis(2-(2-pyrrolyl)indenyl)hafnium dichloride, bis(2-(2-pyridyl)indenyl)hafnium dichloride, bis(2-(2-benzofuryl)indenyl)hafnium dichloride, bis(2-(2-indolyl)indenyl)hafnium dichloride, bis(2-(2-quinolyl)indenyl)hafnium dichloride, bis(2-(2-furyl)-1-methylindenyl)hafnium dichloride, bis(2-(2-furyl)-4-methylindenyl)hafnium dichloride, bis(2-(2-furyl)-4-phenylindenyl)hafnium dichloride, bis(2-(2-furyl)-4-naphthylindenyl)hafnium dichloride, bis(2-(2-furyl)-4,5-benzoindenyl)hafnium dichloride, bis(2-(2-furyl) cyclopentaphenanthryl)hafnium dichloride, bis(2-(2-furyl)indenyl)titanium dichloride, bis(2-(2-furyl)indenyl)titanium dibromide, bis(2-(2-furyl)indenyl)titanium methylchloride, bis(2-(2-furyl)indenyl)titanium dimethyl, bis(2-(2-furyl) indenyl)titanium diphenyl, bis(2-(2-thienyl)indenyl) titanium dichloride, bis(2-(2-pyrrolyl)indenyl)titanium dichloride, bis(2-(2-pyridyl)indenyl)titanium dichloride, bis(2-(2-benzofuryl)indenyl)titanium dichloride, bis(2-(2-indolyl)indenyl)titanium dichloride, bis(2-(2-quinolyl) indenyl)titanium dichloride, bis(2-(2-furyl)-1-methylindenyl)titanium dichloride, bis(2-(2-furyl)-4-methylindenyl)titanium dichloride, bis(2-(2-furyl)-4-phenylindenyl )titanium dichloride, bis(2-(2-furyl)-4-naphthylindenyl)titanium dichloride, bis(2-(2-furyl)-4,5-benzoindenyl)titanium dichloride, bis(2-(2-furyl) cyclopentaphenanthryl)titanium dichloride, bis(2-(2-(5-fluoro)furyl)indenyl)zirconium dichloride, bis(2-(2-(5-fluoro)furyl)-4,5-benzoindenyl)zirconium dichloride, bis(2-(2-(5-fluoro)furyl)-4-phenylindenyl)zirconium dichloride, bis(2-(2-(5-fluoro)furyl)cyclopentaphenanthryl)zirconium dichloride, bis(2-(2-(5-methyl)furyl)cyclopentaphenanthryl) zirconium dichloride, bis(2-(2-(5-trimethylsilyl)furyl) cyclopentaphenanthryl)zirconium dichloride, bis(2-(2-(5-phenyl)furyl)cyclopentaphenanthryl)zirconium dichloride, bis(2-(2-(5-fluoro)furyl)cyclopentaphenanthryl)zirconium dichloride, bis(2-(2-benzofuryl)cyclopentaphenanthryl) zirconium dichloride, (2-(2-(5-methyl)furyl) cyclopentaphenanthryl)(2-(2-(5-methyl)furyl)indenyl) zirconium dichloride, bis(2-(2-(5-methyl)furyl)-5,6-bis (trimethylsilyl)indenyl)zirconium dichloride and bis(2-(2-(5-methyl)furyl)-5,6-bis(trimethylsilyl)indenyl)hafnium dichloride.

As a method for the synthesis of a ligand, known methods can be employed. For example, "Tetrahedron Letters, 35, 4, 633–636, (1994)" discloses 2-furyl indene and 2-thienyl indene. As a method for the synthesis of an indene substituted by a heteroaromatic group, there is a method wherein a halogenated indene and a boronic acid derivative of an heteroaromatic compound are subjected to cross coupling in the presence of a catalyst. For instance, 2-(2-furyl)indene can be synthesized by subjecting 2-bromo indene and 2-furyl boronic acid to cross coupling with a Pd metal in the presence of a base.

A representative synthesis route of the metallocene compound of formula (1) according to the present invention is illustrated below, but not limited thereto.

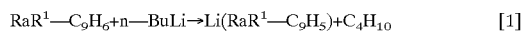

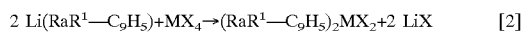

More specifically, the metallocene compound of formula (1) is prepared by a process comprising step [1] of anionizing an indene substituted by a heteroaromatic group with a metal salt type base and step [2] of reacting the anionized, substituted indene, for instance, with a metal halide.

Examples of metal salt type bases used in the anionization of the heteroaromatic group-substituted indene in step [1] can include methyllithium, n-butyllithium, t-butyllithium, phenyllithium, lithium hydride, sodium hydride, potassium hydride, calcium hydride, lithium diisopropylamide, t-butyloxypotassium, methylmagnesium iodide, ethylmagnesium iodide, phenylmagnesium bromide, and t-butylmagnesium bromide.

The anionization reaction of the heteroaromatic group-substituted indene can be carried out with said metal salt type base in the presence of an amine compound which includes primary amines, e.g., methylamine, ethylamine, n-propyl-amine, isopropylamine, n-butylamine, tert-butylamine, aniline and ethylenediamine; secondary amines, e.g., dimethylamine, diethylamine, di-n-propylamine, diisopropylamine, di-n-butylamine, di-tert-butylamine, pyrrolidine, hexamethyldisilazane and diphenylamine; and tertiary amines, e.g., trimethylamine, triethylamine, tri-n-propylamine, triisopropylamine, tri-n-butylamine, tri-tert-butylamine, triphenylamine, N,N-dimethylaniline, N,N,N',N'-tetramethylethylenediamine, N-methylpyrrolidine and 4-dimethylaminopyridine.

The anionization reaction of the substituted indene is usually carried out in an organic solvent at a reaction temperature between not lower than −100° C. and not higher than a boiling point of the solvent used, preferably in the range of −70° C. to 100° C.

The organic solvents used in the reaction can be used without any limitation, unless they are reactive to the starting compounds or reaction products or decompose them. Preferably, ethers, halogenated hydrocarbons or aromatic compounds can be used. For ethers, preferable are relatively low-molecular ethers such as diethylether, diisopropylether, tetrahydrofuran and dimethoxyethane. Dichloromethane is preferable for halogenated hydrocarbons. For aromatic compounds, preferable are toluene, anisol and xylene. Further, a mixed solvent of these two or more compounds can be used.

Examples of metal halides reacted with the anionized, substituted indene in step [2] can include metal tetrahalides or metal tri- or di-halides wherein up to two halogen atoms are substituted by said hydrocarbon group, said halogenated hydrocarbon group or said silyl group, for example, titanium tetrachloride, titanium tetrabromide, titanium tetraiodide, titanium tetrafluoride, titanium trichloride, titanium tribromide, titanium triiodide, titanium trifluoride, zirconium tetrachloride, zirconium tetrabromide, zirconium tetraiodide, zirconium tetrafluoride, hafnium tetrachloride, hafnium tetrabromide, hafnium tetraiodide and hafnium tetrafluoride. Preferable are metal tetrahalides.

The metallocene compound is isolated and purified from the reaction solution after the reaction in step [2] by a conventional method. The purification can be performed by distilling the solvent off, or by extraction with a suitable solvent, adsorption, filtration, recrystallization or the like, as the occasion demands. Usually, a desired product can be crystallized out by utilizing the difference between the desired product and impurities in solubility in a solvent, and further purified by recrystallization or the like to prepare the metallocene compound of the present invention.

The present metallocene compound of the formula (1) used together with aluminoxane, an ionic compound or a mixture of an ionic compound and an organoaluminum compound, as a catalyst for olefin polymerization, exhibits an excellent polymerization activity.

Aluminoxanes are organoaluminum compounds represented by the following formula (2) or (3) or the mixture thereof.

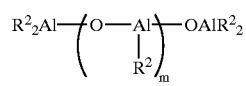
(2)

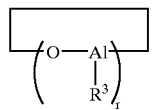
(3)

In the formulae (2) and (3), each $R^2$ and $R^3$ independently represent a hydrogen atom or a hydrocarbon group of 1–20 carbons, m represents an integer of 4–30 and r represents an integer of 6–32.

Examples of the hydrocarbon group of 1–20 carbons can include an alkyl group such as methyl, ethyl, propyl, butyl, isobutyl, pentyl, hexyl, etc.; an alkenyl group such as allyl, 2-methylallyl, propenyl, isopropenyl, 2-methyl-1-propenyl, butenyl, etc.; a cycloalkyl group such as cyclopropyl, cyclobutyl, cyclopentyl, cyclohexyl, etc.; and an aryl group, etc. Preferable is a hydrocarbon group of 1–6 carbons, and more preferable is that of 1–4 carbons.

In the formula (2), m is an integer of 4 to 30, preferably 6 to 30, and more preferably 8 to 30.

In the formula (3), r is an integer of 6 to 32, preferably 8 to 32, and more preferably 10 to 32.

In case where at least two $R^2$'s are identical in the formula (2) and at least two $R^3$'s are identical in the formula (3), each $R^2$ and $R^3$ are independently and preferably a hydrocarbon group such as methyl, ethyl, propyl, isobutyl, phenyl and benzyl, and most preferably methyl.

In case where at least one $R^2$ is not identical in the formula (2) and at least one $R^3$ is not identical in the formula (3), each $R^2$ and $R^3$ are independently and preferably a combination containing methyl and hydrogen or a combination containing methyl and isobutyl, and more preferably a combination consisting of methyl and hydrogen or a combination consisting of methyl and isobutyl. In case where $R^2$ and $R^3$ are composed of a combination consisting of methyl and hydrogen, the proportion of the number of hydrogen to the sum total of methyl and hydrogen is preferably in the range of 0.01–60%. In case where $R^2$ and $R^3$ are composed of a combination consisting of methyl and isobutyl, the proportion of the number of isobutyl to the sum total of methyl and isobutyl is preferably in the range of 0.01–60%.

The above-mentioned aluminoxanes can be prepared by various known methods, examples of which are recited below.

[1] A method of reacting a trialkyl aluminum directly with water in an organic solvent such as toluene and ether;

[2] A method of reacting a trialkyl aluminum with salts containing crystal water, e.g., copper sulfate hydrate and aluminum sulfate hydrate;

[3] A method of reacting a trialkyl aluminum with water impregnated in silica gel or the like;

[4] A method of reacting a mixture of trimethyl aluminum and triisobutyl aluminum directly with water in an organic solvent such as toluene and ether;

[5] A method of reacting a mixture of trimethyl aluminum and triisobutyl aluminum with salts containing crystal water, e.g., copper sulfate hydrate and aluminum sulfate hydrate; and

[6] A method of impregnating water in silica gel or the like, and reacting it with triisobutyl aluminum, and further trimethyl aluminum.

The ionic compounds can be represented by the following formula (4).

$$[C^+][A^-]$$ (4)

wherein [C⁺] represents a cation and [A⁻] represents an anion.

The cation [C⁺] includes those containing an active proton and not containing the proton. The cations containing the active proton can include, for example, Brønsted acid, e.g., trimethylammonium, triethylammonium, tripropylammonium, tributylammonium, N,N-dimethylanilinium, N,N,2,4,5-pentamethylanilinium, triphenylphosphonium, tri(o-tolyl)phosphonium, tri(p-tolyl)phosphonium and tri(mesityl)phosphonium. The cations not containing it can include, for example, carbonium, oxonium and sulfonium cations.

The anions [A⁻] can include, for example, [AlR₄⁻], [BR₄⁻], [PR₆⁻] and [ClO₄⁻]. R represents a hydrocarbon group of 1–20 carbons such as methyl, ethyl, n-propyl, isopropyl, n-butyl, isobutyl, sec-butyl, t-butyl, n-pentyl, isopentyl, sec-pentyl, t-pentyl, hexyl, heptyl, octyl, nonyl, decyl, phenyl, benzyl and naphthyl. R may be substituted by a hydrocarbon group of 1–10 carbons or a halogen atom, examples of which can include methylphenyl, dimethylphenyl, trimethylphenyl, hexamethylphenyl, pentamethylphenyl, ethylphenyl, butylphenyl, pentylphenyl, chlorophenyl, dichlorophenyl, trichlorophenyl, hexachlorophenyl, pentachlorophenyl, bromophenyl, dibromophenyl, tribromophenyl, hexabromophenyl, pentabromophenyl, fluorophenyl, difluorophenyl, trifluorophenyl, hexafluorophenyl and pentafluorophenyl.

An organoaluminum compound which is used together with the ionic compound as a catalyst component in the catalyst for olefin polymerization comprising the metallocene compound of the present invention can be represented by the following formula (5).

$$R^4_s AlY_{3-s} \qquad (5)$$

wherein R⁴ represents a hydrocarbon group of 3–12 carbons, Y represents a hydrogen atom or a halogen atom and s represents an integer of 1–3.

R⁴ can include, for example, an alkyl group such as methyl, ethyl, n-propyl, isopropyl, n-butyl, isobutyl and t-butyl, and an alkenyl group.

The halogen atom for Y can include, for example, fluorine, chlorine and bromine.

In case where the catalyst of the present invention contains the metallocene compound and aluminoxane, it is preferably used in such a range that an aluminum atom in aluminoxane is 10–100000 mols, preferably 50–50000 mols, and most preferably 100–30000 mols per mol of the transition metal atom in the metallocene compound.

The term "polymerization" as used herein means both homopolymerization and copolymerization. Accordingly, the term "olefin polymer" includes a homopolymer of an olefin and a copolymer of two or more olefins.

The catalyst of the present invention can be used in the polymerization of olefins. The olefins which can polymerize can include straight-chain α-olefins such as ethylene, propylene, 1-butene, 4-methyl-1-pentene, 1-hexene, 1-pentene, 1-decene, 1-dodecene, 1-tetradecene, 1-hexadecene, 1-octadecene and 1-eicosene, and branched-chain α-olefins such as 3-methyl-1-butene, 4-methyl-1-pentene and 2-methyl-1-pentene.

A mixture containing two or more olefins can be polymerized by using the catalyst of the present invention. For example, a mixture of two olefins such as ethylene/propylene and propylene/1-butene or a mixture of three olefins such as ethylene/propylene/1-butene can be polymerized to produce a random copolymer.

By employing a multi-stage polymerization process comprising plural polymerization steps and varying kinds of feed olefins in each step, for example, a block copolymer containing two or more olefin units based on the combination of olefins as mentioned above can be produced.

The catalyst of the present invention can also be used in the polymerization of the above olefin and the above mixture of two or more olefins which further contain conjugated or non-conjugated dienes such as butadiene, 1,4-hexadiene, 1,4-pentadiene, 1,7-octadiene and 1,9-decadiene, styrenes, cyclic olefins such as cyclopropene, cyclobutene, norbornene and dicyclopentadiene, and polar vinyl monomers such as acrylates and methacrylates.

The catalysts comprising the metallocene compounds of the present invention can be used in the liquid- and gas-phase polymerizations of olefins.

Solvents used in the liquid-phase polymerization can include hydrocarbon compounds capable of dissolving metallocene compounds, for example, aromatic hydrocarbons such as benzene, toluene, o-xylene, m-xylene, p-xylene, ethylbenzene, butylbenzene, mesitylene and naphthalene. Preferably, toluene and xylene are used.

In case where solvents used in the polymerization cannot dissolve the metallocene compounds, the polymerization of olefins can be carried out in those solvents by employing the process as described in Japanese Patent Kokoku 7-96566 wherein the catalyst is preactivated by previously mixing metallocene compounds with aluminoxanes and ionic compounds or with ionic compounds and organoaluminum compounds in an aromatic hydrocarbon, followed by reacting with small amounts of α-olefins. Examples of such solvents which cannot dissolve the metallocene compounds include aliphatic hydrocarbons such as butane, isobutane, pentane, hexane, heptane, octane, decane, dodecane, hexadecane and octadecane; alicyclic hydrocarbons such as cyclopentane, methylcyclopentane, cyclohexane and cyclooctane; and petroleum fractions such as gasoline, kerosene and gas oil. In particular, aliphatic hydrocarbons are preferable. Further, olefins to be polymerized per se can be used as a solvent in the form of liquefied olefin to carry out the polymerization.

In the use of the catalyst, the present metallocene compounds previously mixed with aluminoxanes or ionic compounds or a mixture of ionic compounds and organoaluminum compounds may be supplied to a reaction system. Alternatively, the catalyst components may be supplied separately to the reaction system.

In the polymerization of olefins using the metallocene compounds of the present invention, the polymerization temperature in the reaction system is preferably from –50° C. to 150° C., most preferably from –10° C. to 100° C., but not limited thereto. The polymerization pressure is preferably in the range of from atmospheric pressure to 7 MPa, most preferably from 0.2 MPa to 5 MPa, but not limited thereto. The molecular weight of olefin polymers to be produced can be regulated by known means, for example, choice of the polymerization temperature or introduction of hydrogen.

The catalysts for olefin polymerization according to the present invention may contain two or more metallocene compounds in any proportion. Further, the catalysts of the present invention may be used in combination with other known catalysts for olefin polymerization in any proportion. The addition of the olefin polymerization catalysts of the present invention can modify olefins produced by using only known olefin polymerization catalyst. In particular, polyolefins having various physical properties can be produced by adding known metallocene compounds to the olefin polymerization catalysts of the present invention in any proportion.

The present invention is further illustrated by the following non-limitative Examples.

The definition of the terms and the method for the measurement of the physical properties used in the Examples and Comparative Examples are mentioned below. Melting point (Tm): It is defined as a temperature showing a peak on melting which was determined by heating an olefin polymer from room temperature to 230° C. at a rate of 30° C./min, keeping it at 230° C. for 10 minutes, followed by lowering to −20° C. at a rate of 20° C./min, keeping it at −20° C. for another 10 minutes and heating it again at a rate of 20° C./min, using DCS 7 type differential scanning calorimeter (manufactured by Perkin Elmer Co., Ltd.). Molecular weight (Mw), molecular weight distribution (Mw/Mn): They were calculated from the result which was measured at 135° C. by a gel permeation chromatography (GPC) (e.g., GPC-150C manufactured by Waters Co., Ltd.) with a mixed polystyrene gel column (e.g., PSK gel GMH6-HT manufactured by Toso K.K.) using a solution of 0.05% by weight of the polymer in o-dichlorobenzene. Isotactic pentad content (mmmm): It was calculated from $^{13}$C-NMR spectra which were determined for a solution of 20% by weight of the polymer in a mixed solvent of o-dichlorobenzene/benzene bromide at 8/2 weight ratio under the condition of 67.20 MHz and 130° C., using a NMR spectrometer (e.g., JEOL-GX270 manufactured by Nihon Densi K.K. in Japan).

Intrinsic viscosity (η): It was measured at 135° C. in a decalin solution, using Ubbellohde viscometer.

EXAMPLE 1

Synthesis of bis(2-(2-furyl)indenyl)zirconium dichloride

A 500-ml glass reaction vessel was charged with 5.0 g (0.028 mol) of 2-(2-furyl)indene and 140 ml of tetrahydrofuran (THF), and the mixture was cooled to −60° C. on a dry ice/methanol bath. 18 ml (0.029 mol) of an n-butyllithium/hexane solution (1.57 mol/L) were added dropwise to the mixture. Subsequently, the mixture was warmed to room temperature and stirred for 18 hrs. to prepare a reddish brown solution. A solvent in the reddish brown solution was concentrated under reduced pressure until the volume was reduced to about 30 ml, 60 ml of toluene were added and the solution was cooled to −50° C. on a dry ice/methanol bath. 3.5 g (0.015 mol) of zirconium tetrachloride suspended in 140 ml of toluene were added. This mixture was warmed to room temperature and stirred for 20 hrs. After completion of the reaction, recrystallization from toluene afforded 1.57 g (21% yield) of a light yellow crystal of bis(2-(2-furyl)indenyl)zirconium dichloride. The structure was confirmed by $^1$H-NMR.

$^1$H-NMR (500 MHz, CDCl$_3$): δ6.55 (dd, 2H), 6.57 (dd, 2H), 6.66 (s, 4H), 7.13 (dd, 4H), 7.28 (dd, 4H), 7.59 (dd, 2H)

EXAMPLE 2

Polymerization of propylene using bis(2-(2-furyl)indenyl)zirconium dichloride

A 1.5-L stainless polymerization reactor equipped with an agitator was purged with nitrogen gas and charged successively with 1 L of toluene, a toluene solution of methyl aluminoxane (available from Toso-Aczo Co., Ltd. under the trade name of MMAO type 3A) in an amount to provide Al/Zr=10000, and 3 ml of a toluene solution containing bis(2-(2-furyl)indenyl)zirconium dichloride (0.0069 mmol) prepared in Example 1, and the mixture was heated to 30° C. Subsequently, propylene was supplied continuously to the reactor so that the pressure within the polymerization reactor was maintained at 0.3 MPa, and the polymerization reaction was carried out for one hour. After completion of the polymerization, unreacted propylene was discharged from the polymerization reactor and a catalyst component was decomposed by placing in hydrochloric acid/methanol. The precipitated polypropylene was washed and dried under reduced pressure to obtain 8.9 g of an elastomeric polypropylene. The analytical values are shown in Table 1.

EXAMPLE 3

Synthesis of bis(2-(2-thienyl)indenyl)zirconium dichloride

A 500-ml glass reaction vessel was charged with 5.0 g (0.025 mol) of 2-(2-thienyl)indene and 140 ml of THF, and the mixture was cooled to −60° C. on a dry ice/methanol bath. 17 ml (0.026 mol) of an n-butyllithium/hexane solution (1.57 mol/L) were added dropwise to the mixture. Subsequently, the mixture was warmed to room temperature and stirred for 18 hrs. to prepare a reddish brown solution. A solvent in the reddish brown solution was concentrated under reduced pressure until the volume was reduced to about 30 ml, 60 ml of toluene were added and the solution was cooled to −15° C. on a dry ice/methanol bath. 3.5 g (0.015 mol) of zirconium tetrachloride suspended in 140 ml of toluene were added. This mixture was warmed to room temperature and stirred for 20 hrs. After completion of the reaction, recrystallization from toluene afforded 1.13 g (16% yield) of a light yellow crystal of bis(2-(2-thienyl)indenyl)zirconium dichloride. The structure was confirmed by $^1$H-NMR.

$^1$H-NMR (500 MHz, CDCl$_3$): δ6.58 (s, 4H), 7.10–7.13 (m, 6H), 7.20–7.22 (m, 6H), 7.39 (dd, 2H)

EXAMPLE 4

Polymerization of propylene using bis(2-(2-thienyl)indenyl)zirconium dichloride

The polymerization was carried out in the same manner as in Example 2, but substituting 3 ml of a toluene solution containing bis(2-(2-thienyl)indenyl)zirconium dichloride (0.0052 mmol) for 3 ml of a toluene solution containing bis(2-(2-furyl)indenyl)zirconium dichloride (0.0069 mmol). 8.9 g of an elastomeric polypropylene were produced. The analytical values of the resultant polypropylene are shown in Table 1.

EXAMPLE 5

Synthesis of bis(2-(2-(4,5-benzofuryl))indenyl)zirconium dichloride

A 500-ml glass reaction vessel was charged with 10.3 g (0.044 mol) of 2-(2-(4,5-benzofuryl))indene and 250 ml of THF, and the mixture was cooled to −60° C. on a dry ice/methanol bath. 30 ml (0.045 mol) of an n-butyllithium/hexane solution (1.50 mol/L) were added dropwise to the mixture. Subsequently, the mixture was warmed to room temperature and stirred for 18 hrs. to prepare a reddish orange solution. A solvent in the reddish orange solution was concentrated under reduced pressure until the volume was reduced to about 30 ml, 200 ml of toluene were added and the solution was cooled to −70° C. on a dry ice/methanol bath. 5.1 g (0.022 mol) of zirconium tetrachloride were added. This mixture was warmed to room temperature and stirred for 20 hrs. After completion of the reaction, recrystallization from dichloromethane/hexane afforded 3.1 g (22% yield) of an orange crystal of bis(2-(2-(4,5-benzofuryl))indenyl)zirconium dichloride. The structure was confirmed by $^1$H-NMR.

$^1$H-NMR (90 MHz, CDCl$_3$): δ6.75 (s, 2H), 6.91 (s, 4H), 7.05–7.57 (m, 16H)

EXAMPLE 6

Polymerization of propylene using bis(2-(2-(4,5-benzofuryl))indenyl)zirconium dichloride The polymerization was carried out in the same manner as in Example 2, but substituting 3 ml of a toluene solution containing bis(2-(2-(4,5-benzofuryl))indenyl)zirconium dichloride (0.0062 mmol) for 3 ml of a toluene solution containing bis(2-(2-furyl)indenyl)zirconium dichloride (0.0069 mmol). 12.1 g of an elastomeric polypropylene were produced. The analytical values of the resultant polypropylene are shown in Table 1.

EXAMPLE 7 synthesis of bis(2-(2-furyl)-4-phenylindenyl) zirconium dichloride

A 500-ml glass reaction vessel was charged with 7.8 g (0.030 mol) of 2-(2-furyl)-4-phenylindene and 150 ml of THF, and the mixture was cooled to −50° C. on a dry ice/methanol bath. 20 ml (0.030 mol) of an n-butyllithium/hexane solution (1.50 mol/L) were added dropwise to the mixture. Subsequently, the mixture was warmed to room temperature and stirred for 18 hrs. to prepare a reddish orange solution.

A solvent in the reddish orange solution was concentrated under reduced pressure until the volume was reduced to about 30 ml, 250 ml of toluene were added and the solution was cooled to −70° C. on a dry ice/methanol bath. 3.5 g (0.015 mol) of zirconium tetrachloride were added. This mixture was warmed to room temperature and stirred for 20 hrs. After completion of the reaction, recrystallization from dichloromethane/hexane afforded two isomers (A, B) of bis(2-(2-furyl)-4-phenylindenyl)zirconium dichloride (Isomer A: orange crystal, 0.68 g, 7% yield; Isomer B: light orange needle crystal, 0.55 g, 5% yield). The structure was confirmed by $^1$H-NMR.

$^1$H-NMR (500 MHz, CDCl$_3$):

Isomer A: δ6.49 (d, 2H), δ6.53 (dd, 2H), δ6.78 (d, 2H), δ6.87 (d, 2H), δ6.99 (d, 2H), δ6.99 (dd, 2H), δ7.23 (d, 2H), δ7.37 (t, 2H), δ7.44 (t, 4H), δ7.56 (d, 2H), δ7.61 (d, 4H)

Isomer B: δ6.42 (dd, 2H), δ6.52 (d, 2H), δ6.67 (d, 2H), δ6.73 (d, 2H), δ7.14–7.26 (m, 6H), δ7.34–7.48 (m, 12H)

EXAMPLE 8

Polymerization of propylene using bis(2-(2-furyl)-4-phenylindenyl)zirconium dichloride The polymerization was carried out in the same manner as in Example 2, but substituting 3 ml of a toluene solution each containing Isomer A (0.0010 mmol) and Isomer B (0.056 mmol) of bis(2-(2-furyl)-4-phenylindenyl)zirconium dichloride for 3 ml of a toluene solution containing bis(2-(2-furyl)indenyl)zirconium dichloride (0.0069 mmol). 1.4 g and 0.7 g of an elastomeric polypropylene were produced, respectively. The analytical values of the resultant polypropylene are shown in Table 1.

EXAMPLE 9

Synthesis of bis(2-(2-(5-methyl)furyl)indenyl) zirconium dichloride

A 500-ml glass reaction vessel was charged with 7.8 g (0.030 mol) of 2-(2-(5-methyl)furyl)indene and 150 ml of diethyl ether, and the mixture was cooled to −50° C. on a dry ice/methanol bath. 17 ml (0.026 mol) of an n-butyllithium/hexane solution (1.50 mol/L) were added dropwise to the mixture. Subsequently, the mixture was stirred for 18 hrs., while gradually warming to room temperature, to prepare a reddish orange solution.

A solvent in the reddish orange solution was concentrated under reduced pressure until the volume was reduced to about 30 ml, 200 ml of toluene were added and the solution was cooled to −70° C. on a dry ice/methanol bath. 3.0 g (0.013 mol) of zirconium tetrachloride were added. This mixture was stirred for 20 hrs., while gradually warming to room temperature. After completion of the reaction, recrystallization from dichloromethane/hexane afforded 1.7 g (24% yield) of an orange crystal of bis(2-(2-(5-methyl)furyl) indenyl)zirconium dichloride. The structure was confirmed by $^1$H-NMR.

$^1$H-NMR (500 MHz, CDCl$_3$): δ2.48 (s, 6H), 6.13 (d, 2H), δ6.45 (d, 2H), δ6.59 (s, 4H), δ7.11 (dd, 4H), δ7.27 (dd, 4H)

EXAMPLE 10

Polymerization of propylene using bis(2-(2-(5-methyl)furyl)indenyl)zirconium dichloride A 1.5-L stainless polymerization reactor equipped with an agitator was purged with nitrogen gas and charged successively with 1 L of toluene, a toluene solution of methyl aluminoxane (available from Toso-Aczo Co., Ltd. under the trade name of MMAO type 3A) in an amount to provide Al/Zr=10000, and 3 ml of a toluene solution containing bis(2-(2-(5-methyl)furyl)indenyl)zirconium dichloride (0.0069 mmol) prepared in Example 9, and the mixture was heated to 30° C. Subsequently, propylene was supplied continuously to the reactor so that the pressure within the polymerization reactor was maintained at 0.3 MPa, and the polymerization reaction was carried out for one hour. After completion of the polymerization, unreacted propylene was discharged from the polymerization reactor and a catalyst component was decomposed by placing in hydrochloric acid/methanol. The precipitated polypropylene was washed and dried under reduced pressure to obtain 8.9 g of an elastomeric polypropylene. The analytical values of the resultant polypropylene are shown in Table 1.

EXAMPLE 11

Synthesis of bis(2-(2-(5-methyl)furyl)cyclopenta(1)-phenanthryl)zirconium dichloride A 500-ml glass reaction vessel was charged with 8.7 g (0.029 mol) of 2-(2-(5-methyl)furyl)cyclopenta(1)-phenanthrene and 200 ml of THF, and the mixture was cooled to −70° C. on a dry ice/methanol bath. 18.5 ml (0.029 mol) of an n-butyllithium/hexane solution (1.59 mol/L) were added dropwise to the mixture. Subsequently, the mixture was stirred for 18 hrs., while gradually warming to room temperature to prepare a deep red solution.

A solvent in the deep red solution was distilled off under reduced pressure, 200 ml of toluene were added and the solution was cooled to −70° C. on a dry ice/methanol bath. 3.4 g (0.015 mol) of zirconium tetrachloride were added.

This mixture was stirred for 20 hrs., while gradually warming to room temperature. After completion of the reaction, recrystallization from dichloromethane/hexane afforded 1.9 g (18% yield) of a yellow crystal of bis(2-(2-(5-methyl)furyl)cyclopenta(1)phenanthryl)zirconium dichloride. The structure was confirmed by $^1$H-NMR.

$^1$H-NMR (500 MHz, CDCl$_3$): δ2.62 (s, 6H), δ6.34 (d, 2H), δ6.57 (d, 2H), δ6.96 (s, 4H), δ7.40 (t, 4H), δ7.49 (t, 4H), δ7.54 (d, 4H), δ8.41 (d, 4H)

Comparative Example 1

Polymerization of propylene using bis(2-phenylindenyl)zirconium dichloride

Bis(2-phenylindenyl)zirconium dichloride was synthesized in accordance with the method disclosed in Japanese Patent Publication 9-510745.

The polymerization was carried out in the same manner as in Example 2, but substituting 3 ml of a toluene solution containing bis(2-phenylindenyl)zirconium dichloride (0.0052 mmol) for 3 ml of a toluene solution containing bis(2-(2-furyl)indenyl)zirconium dichloride (0.0069 mmol). 6.6 g of an elastomeric polypropylene were produced. The analytical values of the resultant polypropylene are shown in Table 1.

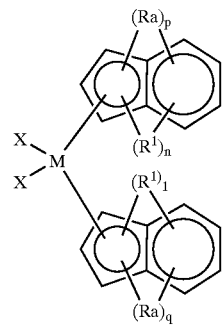

(1)

wherein M represents a transition metal atom in Group 3 including lanthanoid and actinoid series, or Group 4 or 5 of the periodic table;

each Ra independently represents a monocyclic or polycyclic heteroaromatic group containing a heteroatom selected from the group consisting of an oxygen atom, a sulfur atom and a nitrogen atom;

each R$^1$ independently represents a halogen atom, a hydrocarbon group of 1–20 carbons, a halogenated hydrocarbon group of 1–20 carbons, a silyl group

TABLE 1

| | Analytical values of polypropylene | | | | | | | |
|---|---|---|---|---|---|---|---|---|
| | Amount of metallocene used × 10$^{-6}$ mol | Yield g | Activity kg-pp/mmol-M-h | Mw × 10$^4$ | Mw/Mn | [η] | Tm °C. | mmmm |
| Example 2 (2-(2-Furyl)Ind)$_2$ZrCl$_2$ | 6.9 | 8.9 | 1.3 | 9.1 | 2.31 | 0.81 | 153.3 | 0.211 |
| Example 4 (2-(2-Thienyl)Ind)$_2$ZrCl$_2$ | 5.2 | 4.0 | 0.8 | 7.5 | 3.45 | 0.74 | — | 0.196 |
| Example 6 (2-(2-Benzofuryl)Ind)$_2$ZrCl$_2$ | 6.2 | 12.1 | 2.0 | 9.4 | 2.5 | 0.87 | 140.8 | 0.383 |
| Example 8 (2-(2-Furyl)-4-Ph-Ind)$_2$ZrCl$_2$ | 1.0 | 1.44 | 1.4 | 20.2 | 3.84 | 1.57 | 95.1 | 0.610 |
| (2-(2-Furyl)-4-Ph-Ind)$_2$ZrCl$_2$ | 5.6 | 0.7 | 0.1 | 5.8 | 2.93 | 0.56 | 108.2 | 0.372 |
| Example 10 (2-(2-(5-Me)Furyl)Ind)$_2$ZrCl$_2$ | 6.7 | 2.26 | 0.3 | 11.5 | 3.00 | 0.96 | 128.0 | 0.357 |
| Comparative Example 1 (2-PhInd)$_2$ZrCl$_2$ | 10.1 | 6.6 | 0.65 | 10.4 | 2.74 | 1.00 | 130.4 | 0.197 |

EFFECT OF THE INVENTION

The present invention can provide new metallocene compounds which can efficiently produce elastomeric polyolefins, and also provide catalysts containing the same. Elastomeric polyolefins with a high heat resistance can be produced by using metallocene compounds wherein a furyl group is introduced at the 2-position of the indenyl ligand. Further, polyolefins with high stereoregularity and high molecular weight can be produced by using metallocene compounds wherein the substituent is introduced preferably at the 5-position of the furyl group and the substituent is introduced preferably at the 4-position of the indenyl group.

What is claimed is:

1. A metallocene compound having an indenyl ligand represented by the following formula (1)

substituted by said hydrocarbon group or said halogenated hydrocarbon group, an amino group substituted by said hydrocarbon group, or a monocyclic or polycyclic amino group, and adjacent R$^1$'s may be joined together to form a ring of 6–8 carbons;

p and q are each independently an integer of 1–7;

n and l are each independently 0 or an integer of 1–6; and

X each independently represents a halogen atom, a hydrocarbon group of 1–20 carbons, a halogenated hydrocarbon group of 1–20 carbons, or a silyl group substituted by said hydrocarbon group or said halogenated hydrocarbon group.

2. The metallocene compound of claim 1 wherein M is titanium, zirconium or hafnium.

3. The metallocene compound of claim 1 wherein at least one of Ra is bonded to a 5-membered ring of the indenyl ligand.

4. The metallocene compound of claim 1 wherein at least one of Ra is bonded at the 2-position Of the indenyl ligand.

5. The metallocene compound of claim 1 wherein each Ra independently represents a heteroaromatic group selected from the group consisting of furyl, thienyl, pyridyl, benzofuryl, benzothienyl, quinolyl, pyrrolyl and indolyl.

6. The metallocene compound of claim 1 wherein two of Ra's are furyl and each furyl is bonded at the 2-position of two indenyl ligands.

7. The metallocene compound of claim 1 wherein each $R^1$ independently represents an alkyl group of 1–20 carbons, an aryl group of 6–20 carbons, an aralkyl group of 7–20 carbons, an alkoxy group of 1–20 carbons, an aryloxy group of 6–20 carbons or an aralkyloxy group of 7–20 carbons.

8. A catalyst for olefin polymerization comprising the metallocene compound of claim 1 and a catalyst component selected from the group consisting of aluminoxane, an ionic compound and a mixture of an ionic compound and an organoaluminum compound.

9. The metallocene compound of claim 1, wherein at least one Ra is a monocyclic or polycyclic heteroaromatic group containing an oxygen atom.

10. The metallocene compound of claim 1, wherein at least one Ra is a furyl group.

11. The metallocene compound of claim 1, wherein at least one Ra is a benzofuryl group.

12. The metallocene compound of claim 1, wherein at least one Ra is a 2-furyl group or 3-furyl group.

13. The metallocene compound of claim 1, wherein at least one Ra is a monocyclic or polycyclic heteroaromatic group containing a sulfur atom.

14. The metallocene compound of claim 1, wherein at least one Ra is a heteroaromatic group selected from the group consisting of thienyl and benzothienyl.

15. The metallocene compound of claim 1, wherein at least one Ra is a 2-thienyl group or 3-thienyl group.

16. The metallocene compound of claim 1, wherein at least one Ra is a monocyclic or polycyclic heteroaromatic group containing a nitrogen atom.

17. The metallocene compound of claim 1, wherein at least one Ra is a heteroaromatic group selected from the group consisting of pyrrolyl, pyridyl, indolyl, and quinolyl.

18. The metallocene compound of claim 1, wherein at least one Ra is a heteroaromatic group selected from the group consisting of 1-pyrrolyl, 2-pyrrolyl, 3-pyrrolyl, 2-pyridyl, 3-pyridyl, 4-pyridyl, 1-indolyl, 3-indolyl, 1-quinolyl, and 3-quinolyl.

19. The metallocene compound of claim 1, wherein p and q each independently represent an integer of 1–3.

20. The metallocene compound of claim 1, wherein n and l each independently represent 0 or an integer of 1–4.

* * * * *